United States Patent [19]

Carceller et al.

[11] Patent Number: 4,980,362

[45] Date of Patent: Dec. 25, 1990

[54] NEW 4-SUBSTITUTED 2-ALKOXYTETRAHYDROFURAN DERIVATIVES

[75] Inventors: Elena Carceller; Javier Bartroli', both of Barcelona, Spain

[73] Assignee: J. Uriach & CIA. S.A., Barcelona, Spain

[21] Appl. No.: 472,497

[22] Filed: Jan. 30, 1990

[30] Foreign Application Priority Data

Jan. 30, 1990 [ES] Spain .................................. 8900303

[51] Int. Cl.$^5$ ..................... C07D 405/12; A61K 31/44
[52] U.S. Cl. ...................................... 514/336; 546/283
[58] Field of Search ......................... 546/283; 514/336

[56] References Cited

U.S. PATENT DOCUMENTS

| | | | |
|---|---|---|---|
| 4,675,390 | 6/1987 | Bonjouklian et al. | 536/4.1 |
| 4,820,718 | 4/1989 | Tomesch | 546/283 |

FOREIGN PATENT DOCUMENTS

| | | | |
|---|---|---|---|
| 138559 | 4/1985 | European Pat. Off. | |
| 146258 | 6/1985 | European Pat. Off. | |
| 147768 | 7/1985 | European Pat. Off. | |
| 157609 | 10/1985 | European Pat. Off. | |
| 178261 | 4/1986 | European Pat. Off. | |
| 209239 | 1/1987 | European Pat. Off. | |
| 210804 | 2/1987 | European Pat. Off. | |
| 251827 | 1/1988 | European Pat. Off. | |
| 0312040 | 4/1989 | European Pat. Off. | 546/283 |
| 57-165394 | 4/1981 | Japan . | |
| 5835116 | 8/1981 | Japan . | |
| WO86/01507 | 3/1986 | PCT Int'l Appl. | |
| 2186877 | 8/1987 | United Kingdom . | |
| 2200634 | 8/1988 | United Kingdom . | |

*Primary Examiner*—Mary C. Lee
*Assistant Examiner*—Lenora Miltenberger
*Attorney, Agent, or Firm*—Bernard, Rothwell & Brown

[57] ABSTRACT

The present invention describes a process to obtain 4-substituted 2-alkoxytetrahydrofuran derivatives of formula I,

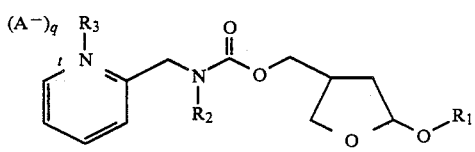

wherein, —$R_1$ represents an alkyl or phenylalkyl radical; —$R_2$ is hydrogen, $C_1$–$C_4$-acryl or $C_1$–$C_4$-alkoxycarbonyl; —$R_3$ is either an electron pair, in which case t means nothing and q is zero, or $R_3$ is hydrogen or $C_1$–$C_4$ alkyl, in which case t is (+) and q=1; A— is a pharmaceutically acceptable anion. These compounds are antagonists of PAF and, therefore, useful for the treatment of the diseases in which this substance is involved.

11 Claims, No Drawings

NEW 4-SUBSTITUTED 2-ALKOXYTETRAHYDROFURAN DERIVATIVES

FIELD OF THE INVENTION

The present invention relates to new 4-substituted 2-alkoxytetrahydrofuran derivatives with a potent antagonist activity of the platelet activating factor (PAF), together with a process for their preparation. The invention also relates to the pharmaceutical preparations which contain these compounds an their use in the treatment of diseases in which PAF is involved, such as allergic and bronchial asthma, platelet aggregation disorders, septic shock, hypertension, etc.

BRIEF DESCRIPTION OF THE PRIOR ART

The platelet activating factor (PAF) or (1-O-alkyl-2-acetyl-sn-glyceryl-3-phosphorylcholine), also called acetyl glyceryl ether phosphorylcholine (AGEPC) or PAF-acether is a natural phospholipid synthesized by different cells (basophiles, macrophages, neutrophiles, platelets) and tissues (heart, lung and kidney) of the organism (Roubin et al. in "Lymphokines" Ed. E. Pick, Acad. Press. New York, p. 249, 1983; Vargaftig et al, Ann. New York Acad. Sci., 1981, 370, 119; Pinckard et al., Int. Arch. Allergy Appl. Immun., 1981, 66, 127).

PAF was described for the first time as a potent platelet aggregating agent (Benveniste et al., J. Exp. Med., 1972, 136) and later it was demonstrated to have other biological activities in vivo, such as peripheral vasodilatation, increase of the vascular permeability, induction of bronchoconstriction and hyperreactivity of the respiratory tract (Mazzoni et al. Proc. Physiol. Soc. Univ. Coll. Meet., March 1985). PAF also produces immediate hypotension followed by pulmonary and renal hypertension in rats (Blank et al., Biochem. Biophis. Res. Commun., 1979, 90, 1194), guinea pigs (Feuerstein, et al., Circul. Shock, 1984, 13, 255), rabbits (Muirhead et al., Hypertension, 1981, 3, 107) and dogs (Otsuka et al., Prostaglandins Leukotrienes Med., 1985, 19, 25), and it has been rated as the most potent ulcerogenic agent described until now.

Consequently, PAF is a mediator that is implicated in a large set of pathological processes such as asthma, septic shock, transplant rejection, thrombosis, ulceration, inflammation and renal diseases.

Even though its mechanism of action is still not known with precision, some studies show that the biological activities of PAF involve the existence of a specific receptor. Recently, it has been possible the isolation of one of these receptors from human platelets and it has been identified as a protein with a molecular weight of 160.000 daltons (Nishihira et al., Tohoku J. Exp. Med., 1985, 147, 145). On the other hand, the capacity to inhibit the binding of $^3$H-PAF to their receptors is well correlated with the amount of PAF needed to provoke the in vitro and in vivo observed effects. These facts indicate that the compounds that act as specific antagonists of PAF could result of interest for the treatment of all those pathological processes related directly or indirectly with PAF.

Until now, several PAF analoges have been investigated in order to find compounds with the antagonist activity above mentioned, for example, the compounds described in patent Nos. EP 147768, EP 146258, EP 138559, EP 157609JP 57/165394, JP 58/133116, JP 58/35116, EP 0209239, EP 0146258, WO 86/01507, EP 210804, EP 0178261, U.S. Pat. No. 4,675,390 among others.

Our invention ES No. 87 02900 describes 2,4-disubstituted tetrahydrofuran derivatives and 5-oxotetrahydrofuran derivatives in which the 4 position of the ring is always substituted by an alkyl chain and the 2 position has a group of formula —CH$_2$O—Y—(CH$_2$)$_n$—$^+$NR$_1$R$_2$R$_3$, where Y is a single bond, or one of the groups —C(=O)—, —C(=O)O—, —C(=O)NH—, —C(=O)NR$_4$—, or —P(=O)(O$_y$)O—, where R$_4$ is a lower alkyl or acyl group, y is (−) or H, n is an integer from 2 to 10, and R$_1$, R$_2$ and R$_3$ are lower alkyl groups or R$_1$R$_2$R$_3$N$^+$ represents an heterocycle.

Our invention ES No. 88 02276 describes tetrahydrofuran derivatives substituted by —CH$_2$OR$_1$ and —CH$_2$OR$_2$ groups in positions 2 and 4 or 4 and 2, wherein R$_1$ represents an alkyl or alkylaminocarbonyl radical; R$_2$ represents a radical of formula —Y—(CH$_2$)n—Q·(A$^-$)$_q$ wherein —Y— is a covalent bond, a carbonyl or a carbonylamino group; n is an integer from 0 to 10; Q is a nitrogenated heterocycle; q is 1 or 0 depending if Q is charged or neutral respectively and A$^-$ is a pharmaceutically acceptable anion.

The present invention describes 2-alkoxytetrahydrofuran derivatives carrying a substituent in the 4 position of the ring. These new compounds show a PAF antagonist activity superior or similar to that of the compounds described in the patent Nos. ES 87 02900 and ES 88 02276 with a greater lasting effect and better oral absorption.

DESCRIPTION OF THE INVENTION

The present invention relates to 4-substituted derivatives of 2-alkoxytetrahydrofuran having the general formula I:

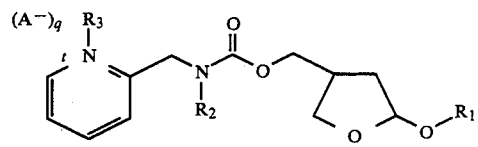

wherein:
— R$_1$ is a linear or branched alkyl, alkenyl or alkynyl group, of 1 to 24 carbon atoms, or a phenyl-(C$_1$-C$_4$)alkyl group;
— R$_2$ is hydrogen, C$_1$-C$_4$-acyl or C$_1$-C$_4$-alkoxycarbonyl;
— R$_3$ is either an electron pair, in which case t means nothing and q is zero, or R$_3$ is hydrogen or C$_1$-C$_4$ alkyl, in which case t is (+) and q=1;
— A$^-$ is a pharmaceutically acceptable anion.

Preferred compounds of formula I are those wherein
— R$_1$ is n-(C$_{12}$-C$_{20}$)alkyl, linear or branched (C$_1$-C$_6$)alkyl, or phenyl-n-(C$_2$-C$_4$)alkyl;
— R$_2$ is hydrogen or C$_1$-C$_3$-acyl;
— R$_3$ is hydrogen or C$_1$-C$_4$ alkyl;
— t is (+) and q=1;
— A$^-$ is chloride, bromide, or iodide.

More preferred compounds of formula I are those wherein
— R$_1$ is n-(C$_{16}$-C$_{18}$)alkyl, linear or branched (C$_2$-C$_5$)alkyl, or phenyl-n-(C$_2$-C$_4$)alkyl;
— R$_2$ is C$_1$-C$_3$-acyl;
— R$_3$ is C$_1$-C$_4$ alkyl;
— t is (+) and q=1;
— A$^-$ is chloride or iodide.

Especially preferred compounds of formula I are those wherein
- $R_1$ is n-$(C_{16}-C_{18})$alkyl, linear or branched $(C_2-C_5)$alkyl, or phenyl-n-$(C_2-C_4)$alkyl;
- $R_2$ is acetyl;
- $R_3$ is ethyl;
- t is (+) and q=1;
- $A^-$ is chloride or iodide.

Compounds of formula I have at least two asymmetric carbons, which can give rise to stereoisomers. The present invention includes these stereoisomers as well as their mixtures.

Although the present invention includes all of the above mentioned compounds, among them are specially preferred the specific compounds whose formulaes are represented below together with the number corresponding to the example in which their preparation is described:

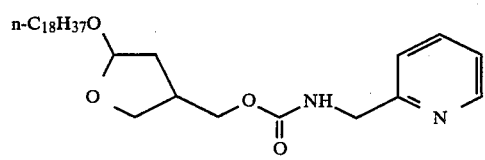
1

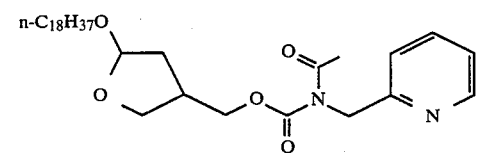
2

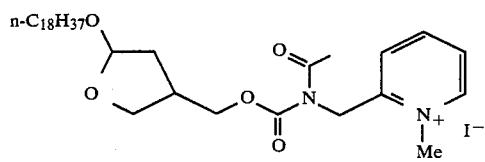
3

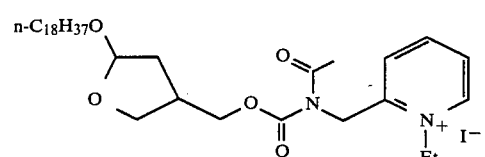
4

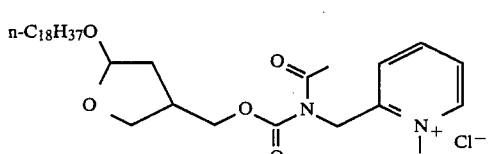
5

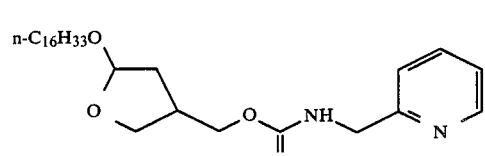
6

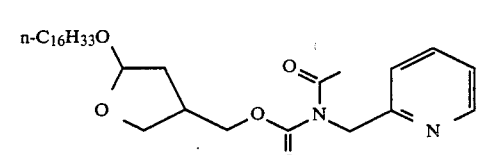
7

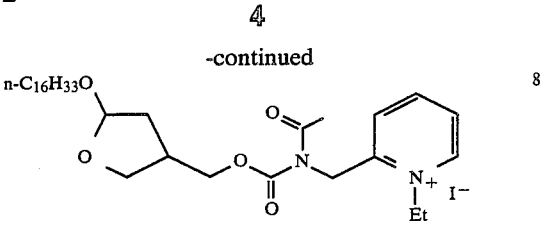
8

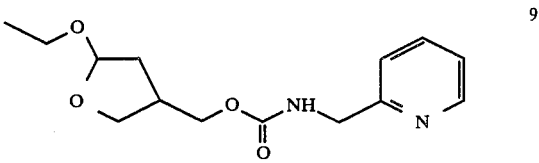
9

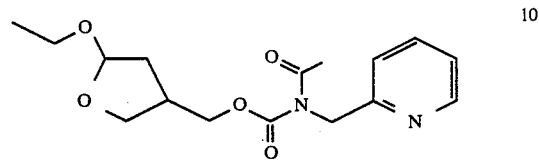
10

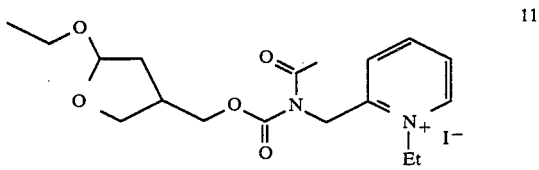
11

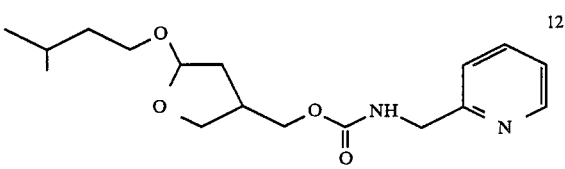
12

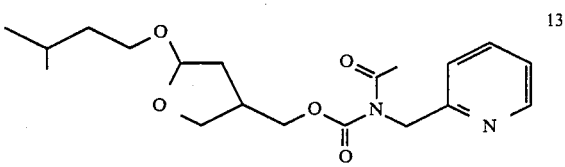
13

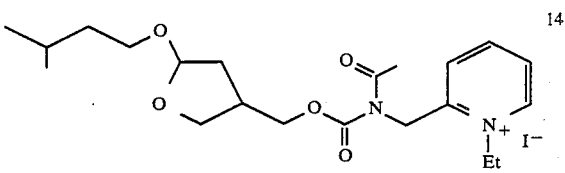
14

15

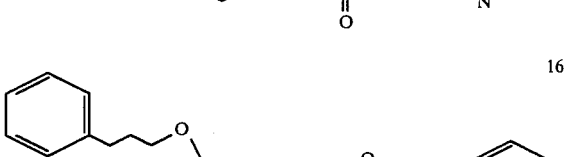
16

-continued

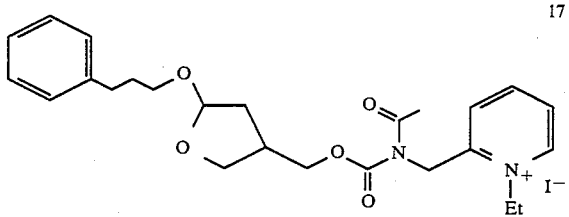

17

The compounds of the present invention are in vitro inhibitors of the platelet aggregation induced by PAF. On the other hand, these compounds have the capacity to revert the hypotension induced by PAF in anesthetized rats. These facts make them useful as PAF antagonists in the treatment of the diseases in which this substance is involved.

The object of the present invention is to provide the compounds having the formula I. Scheme I shows the synthesis of the compounds of formula Ia, that is the compounds of formula I where $R_2$=H and $R_3$=electron pair; Ib (I where, $R_2$=$C_1$-$C_4$-acyl or $C_1$-$C_4$-alkoxycarbonyl, $R_3$=electron pair); and Ic resulting from the quaternization of the pyridyl radical present in Ib.

In step A, the compound of formula IV, that can be easily obtained from diethyl malonate and the diethyl acetal of 2-bromoethanal according to the procedure described in the literature (J. Gen. Chem. USSR 1952, 22, 521), is allowed to react with a reducing agent, such as lithium aluminum hydride, to afford the diol. III. The reaction is usually carried out in a solvent the nature of which is not critical, provided that does not interfere with the reagents; examples of suitable solvents include tetrahydrofuran and diethylether. The reaction will take place over a wide range of temperatures and reaction times. We have found that the reaction can be conveniently done between 0° C. and the temperature of the refluxing solvent, over a period of time from 3 to 24 hours. Once the reaction is complete, the compound of formula III can be isolated by convenient methods such as flash chromatography or distillation.

Scheme I

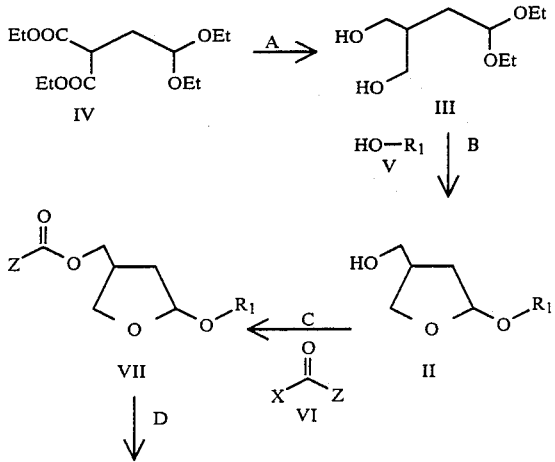

-continued
Scheme I

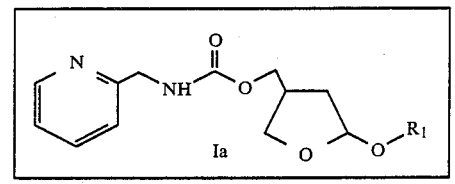

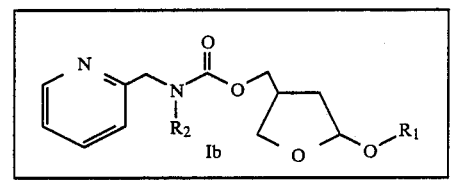

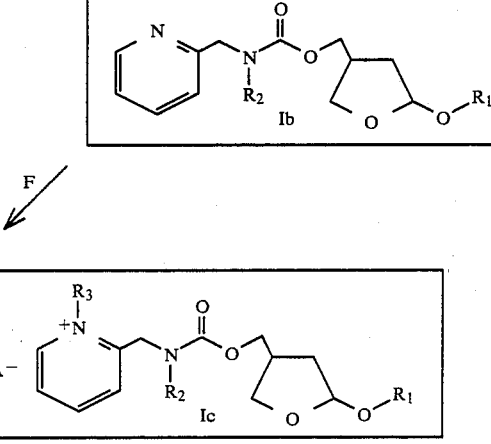

In step B, diol III is treated with a Lewis acid, such as boron trifluoride etherate, or a mineral acid such as trifluoroacetic or hydrochloric acid, in the presence of an alcohol V (where $R_1$ has the previously defined meaning). The reaction is performed in a solvent compatible with the reagents, for instance dichloromethane or chloroform, at a temperature from $-20°$ C. to room temperature, over a period of time from 6 to 72 hours. Once the reaction is complete, the alcohol II can be isolated and purified by convenient methods such as flash chromatography or distillation.

In step C, the alcohol II is allowed to react with a compound VI, one of the so-called phosgene equivalents, that is a doubly activated carbonyl group. In compound VI, the groups X and Z are leaving groups and can be both the same (Cl, imidazole, etc.) or different. Although in principle any phosgene equivalent described in the literature could be used, we have found that phenyl chlorocarbonate (VI, X=Cl, Z=OPh) is an excellent reagent to carry out this reaction, due to its convenience to handle, and its low cost. The reaction is performed in a solvent in the presence of a proton scavenger base. There is no particular restriction on the nature of the solvent to be employed, provided that it does not interfere with other parts of the molecule and that it can dissolve the starting materials at least to some extent. Examples of suitable solvents include halogenated hydrocarbons, particularly, dichloromethane and chloroform; ethers, like diethylether, tetrahydrofuran or dioxane; and aromatic hydrocarbons, like benzene or toluene. Neither any particular restriction exists with respect to the base to be employed, provided that it does not interfere with other functionalities of the molecule. It is preferred to use an amine, such as triethylamine or pyridine. The reaction will take place over a wide range of temperatures and the precise temperature is not particularly critical to the invention. We generally find it convenient to conduct the reaction at a temperature from 0° to 100° C., but temperatures from 0° to 50° C. are preferred. The reaction time required for the reaction can range according to the nature of the starting materials, the base and the temperature used. A period between 30 min and 24 hours is usually satisfactory. The reaction is clean and usually a purification of the product is not necessary. However, if desired, the product VII can be purified by flash chromatography.

In step D, compound VII (obtained in step C) is converted in the carbamate Ia by reaction with 2-(aminomethyl)pyridine. The reaction can be performed in a solvent at a temperature and for a period of time similar to those described in step C. The reaction crude is washed, in this case, with an alkaline aqueous solution in order to take off the phenol produced during the reaction. The product obtained Ia can be purified by conventional methods such as flash chromatography.

Step E involves the derivatization of the carbamic nitrogen of compound Ia to give compound Ib. The reaction involves the use of a reagent of formula $R_2$-X where $R_2$ and X have the previous meaning. In the case in which $R_2$ is acyl, a compound of formula $(R_2)_2O$ can also be used. The reaction can be carried out in two ways, either directly using the compound Ia or preparing first an alkaline salt of it. When compound Ia is used directly, the reaction is performed in a solvent, the nature of which is not critical provided that it is compatible with the reagents used. We have found that the halogenated hydrocarbon solvents such as dichloromethane or chloroform are suitable in this reaction. On the other hand, the reaction can be done in the presence of a proton scavenger amine, such as triethylamine. The use of the amine is not compulsory because the compound itself has a basic nitrogen. The reaction is done in a broad range of temperatures, from 0° C. to the boiling point of the solvent used, but a temperature near room temperature is usually preferred. The time required for the reaction may vary widely depending on many factors, notably the temperature and nature of the starting materials used, however, a period of time from 2 to 72 hours is usually enough. After completion of the reaction, the desired product, of formula Ib, can be isolated and purified by conventional methods such as flash chromatography.

In the case in which an alkaline salt of the compound Ia is used, this salt is formed in the same reaction medium by using a strong base such as sodium hydride or n-butyllithium. The compound $R_2X$ is subsequently added to the same reaction mixture. The reaction is preferently carried out in a solvent the nature of which is not critical, provided that it does not interfere with the reagents. As examples of preferred solvents can be mentioned ethers like diethyl ether, tetrahydrofuran or dioxane; and aromatic hydrocarbons like benzene or toluene. The reaction can be performed in a wide range of temperatures, although we have found that it is better to carry it out at low temperatures, for instance from $-78°$ C. to 0° C., if an acceptable yield is desired. The reaction time depends mainly on the temperature and the nature of the reagents. A period of time from 5 minutes to 2 hours is usually enough. The desired product can be isolated and purified by conventional methodology.

Step F involves the quaternization of the pyridinic nitrogen present in Ib. The reaction is carried out between the starting material and a reagent of formula $R_3A$ where $R_3$ is a lower alkyl group. The reaction can be carried out without solvent in the case in which $R_3A$ is a high boiling point liquid, or in the presence of a solvent when $R_3A$ is either a solid or a low boiling point liquid, but in either case, an excess of reagent is always used. Examples of suitable solvents include those with high polarity. As examples of preferred solvents, we can mention acetonitrile, tetrahydrofuran, dioxane, dimethylformamide or dimethyl sulfoxide. The reaction will take place over a wide range of temperatures and the precise temperature chosen is not particularly critical. We have found convenient to carry it out at a temperature from room temperature to 120° C. The time required for the reaction depends on many factors, notably the nature of the reagent $R_3A$ and the temperature used, but a period of time from 1 to 72 hours is usually satisfactory. The desired compound can be isolated by concentration of the crude reaction or precipitation with a less polar solvent. The compound obtained in this way is usually pure by TLC means. If that is not the case, it can be purified by conventional techniques such as flash chromatography or recrystallization.

Compounds of formula Ic are salts wherein the anion $A^-$ derives from the reagent $R_3A$. If desired, such anion can be changed by using an ionic interchange resin.

Compounds of general formula I are useful as a PAF inhibitors, as demonstrated by their ability to inhibit in vitro platelet aggregation induced by PAF in rabbit according to test 1

Test 1: Inhibition of platelet aggregation induced by PAF.

The blood is obtained by cardiac puncture of male New Zealand albino rabbits (between 2 and 2.5 Kg of weight) and coagulation is prevented by adding 1 part of 3.16% sodium citrate dihydrate in 9 parts of blood. The platelet rich plasma (PRP) is prepared by blood centrifugation at $250 \times g$ for 10 min. at 4° C. and it is diluted with platelet poor plasma (PPP) by additional centrifugation at $3000 \times g$ for 10 min. The amount of platelets is adjusted to $3 \times 10^{-5}/mm^3$. The platelet aggregation induced by PAF ($C_{18}$; prepared in our laboratory) (16 nM, final) is determined by the Born nephelometric technique (J. Physiol., 1962, 162, 67) using a aggregometer Chrono-log 500. The activities of the inhibitors are expressed as $IC_{50}$, that is to say the concentration of the drug needed to inhibit the platelet aggregation by 50%. The results are shown in table 1:

TABLE 1

| Compound number | $IC_{50}(\mu M)$ |
|---|---|
| 3 | 0.045 |
| 4 | 0.016 |
| 5 | 0.012 |
| 8 | 0.012 |
| 11 | 2.9 |
| 14 | 0.7 |
| 17 | 0.19 |

Furthermore, it has been found that the title compounds I are inhibitors of the hypotension induced by PAF according to test 2.

Test 2 - Inhibition of the hypotensive effect induced by PAF in normotense rats.

Male Sprage Dawley rats, of 180–220 g of weight, anesthetized with sodium pentobarbital (50 mg/Kg, i.p. 1 mL/100 g) have been used. In order to measure the average arterial pressure, a polyethylene catheter is introduced into the carotid artery. The arterial pressure is recorded with the help of a transducer connected with a R611 Beckman polygraph. The tested compounds are administered through the femoral vein 3 min before the injection of PAF (0.5 mcg/Kg, i.v.). The inhibition of the hypotension induced by PAF of the different compounds expressed as $IC_{50}$, is shown in table 2.

TABLE 2

| Compound number | $CI_{50}$ (mg/Kg, i.v.) |
| --- | --- |
| 3 | 0.08 |
| 4 | 0.053 |
| 5 | 0.024 |
| 8 | 0.01 |
| 11 | 2.3 |
| 14 | 0.21 |
| 17 | 0.12 |

Finally, certain compounds of the present invention show an improved oral activity with regard to other chemically related PAF-antagonists reported in the literature, such as CV-6209, (disclosed in EP No. 157609) as shown by test 3:

Test 3 - PAF-induced mortality in mice (p.o.)

The experiment is carried out according to the method of Young et al. (Prostaglandins, 1985, 30, 545–551). Groups of 10 Swiss mice weighing 22–26 g are used. 100 mcg/kg of $C_{18}$-PAF plus 1 mg/kg of propanolol are intravenously administered in a lateral tail vein 1 hour after the oral administration of test compounds (0.1 mL/10 g). Every animal is observed 2 hours after the PAF injection. Percent inhibition of mortality due to treatments in comparison with control group are recorded. Results are given as $ID_{50}$ values (mg/kg) in table 3.

TABLE 3

| Compound number | $ID_{50}$ (mg/Kg, p.o.) |
| --- | --- |
| 3 | >100 |
| 4 | 14 |
| 5 | 19 |
| 8 | 80 |
| CV-6209 | 70 |

Solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xanthan gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also administered in the form of suppositories for rectal administration of the drug, or as creams, ointments, jellies, solutions or suspensions for topical use and pessaries for vaginal administration.

The dosage and frequency of dose may vary depending upon symptoms, age and body weight of the patient, as well as upon the route of administration, but, in general, the compounds of the invention may be administered orally in a daily dose of from 50 to 2,000 mg for an adult, preferably a dosage of from 100 to 600 mg, which may be administered either as a single dose or as divided doses.

Following are some representative preparations for tablets capsules, syrups, aerosols and injectables. They can be prepared following standard procedures and they are useful as inhibitors of the platelet activating factor.

| Tablets | |
|---|---|
| Title compound I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Title compound I | 100 mg |
| Lactose | 197 mg |
| Magnesium stearate | 3 mg |
| | 300 mg |
| Syrup | |
| Title compound I | 0,4 g |
| Sucrose | 45 g |
| Flavoring agent | 0,2 g |
| Sweetening agent | 0,1 g |
| Water to | 100 mL |
| Aerosol | |
| Title compound I | 4 g |
| Flavoring agent | 0,2 g |
| Propylene glycol to | 100 mL |
| Suitable propellent to | 1 unit |
| Injectable preparation | |
| Title compound I | 100 mg |
| Benzylic alcohol | 0,05 mL |
| Propylene glycol | 1 mL |
| Water to | 5 mL |

The following examples illustrate, but do not limit, the preparation of the compounds of the present invention.

EXAMPLE 1

(±)-cis,trans-2-[N-[[[(2-octadecyloxytetrahydrofuran-4-yl)methoxy]carbonyl]amino]methyl]pyridine (a) 3-hydroxymethyl-4-hydroxybutanal diethyl acetal.

To a cooled suspension (0° C.) of lithium aluminum hydride (4.9 g, 0.129 mol) in anhydrous tetrahydrofuran (80 mL), was added a solution of diethyl 2,2-diethoxyethylmalonate (17.6 g, 63.7 mmol) in anhydrous tetrahydrofuran (60 mL), and the mixture was stirred 3 h at room temperature. Then, the reaction mixture was immersed in an ice bath and a mixture of water (4.6 mL) and tetrahydrofuran (9.2 mL) was added dropwise followed by a solution of 15% sodium hydroxide (4.6 mL) and water (12.5 mL). After stirring for 20 minutes, the suspension was filtered off, the solvent was removed at reduced pressure, and 300 mL of chloroform was added. The solution was dried over sodium sulfate and after removal of the solvent, 8.8 g of a white solid was obtained and used in the next step without further purification.

IR(film) $\nu$: 3391, 2971, 2927, 2879, 1606, 1373, 1126, 1048, 997 cm$^{-1}$ $^1$H RMN (CDCl$_3$, 60 Mz) $\delta$: 1.18(t,J=7.0 Hz, 6H), 1.7 (m, 3H), 3.45 (m, 3H), 3.45 (m, 8H), 4.6 (t,J=5.3 Hz, 1H).

(b)
(±)-cis,trans-(2-octadecyloxytetrahydrofuran-4-yl)methanol

To a cooled solution (ice/salt bath) of boron trifluoride etherate (1.1 mL) in anhydrous dichloromethane (150 mL) was added, under argon, a solution of the compound obtained in the example 1a (1.4 g, 7.3 mmol) and octadecanol (4.6 g, 17 mmol) in dichloromethane (50 mL). The resulting solution was stirred 18 h at 4° C.

Then, 3 mL of triethylamine was added and the solvents removed under vacuum. The resulting crude reaction was purified by chromatography (silica gel, hexane:ethyl acetate 15%) affording 1.5 g of the desired compound (40% yield) as a 1:1 mixture of cis and trans isomers.

IR(KBr) $\nu$:, 3395, 2914, 2846, 1467, 1087 cm$^{-1}$ $^1$H NMR (CDCl$_3$, 80 MHz) $\delta$: 0.9 (m, 3H), 1.35 (m, 38H), 2.20 (m, 3H), 2.60 (m, 1H), 3.2-4.1 (complex signal, 6H), 5.10 (m, 1H) ppm.

(c) Preparation of the title compound of this example.

To a cooled solution (0° C.) of the compound prepared in example 1b (1.77 g, 4.8 mmol) in dichloromethane (15 mL) were added pyridine (0.75 mL) and phenyl chloroformate (0.75 mL) and the mixture was stirred at room temperature for 1 hour. Then the solution was diluted with dichloromethane and washed first with water and then with 1% sodium bicarbonate. The solution was dried over sodium sulfate and the solvents were removed to afford 2.49 g of the corresponding crude carbonate (Rf=0.66, silica gel, hexane:ethyl acetate 1:1).

To this crude reaction dissolved in acetonitrile (15 mL) was added 2-(aminomethyl)pyridine (0.8 mL) and the resulting mixture was heated to reflux 12 hours. After cooling, the solvents were removed and the residue was treated with chloroform (140 mL) and water (50 mL). The organic phase was washed twice with 1N sodium hydroxide, and dried over sodium sulfate. Removal of the solvent afforded 2.8 g of the title compound as a white solid (quantitative yield).

IR(KBr) $\nu$: 3326, 2957, 2912, 2845, 1702, 1589, 1524, 1463, 1259, 1089 cm$^{-1}$ $^1$H NMR (80 MHz, CDCl$_3$) $\delta$ (TMS): 0.8 (m, 3H), 1.18 (m, 37H), 2.5 (m, 1H), 3.1-4.1 (complex signal, 6H), 4.39 (d,J=5.6 Hz, 2H), 5.00 (m, 1H), 5.85 (1H, NH), 7.12 (m, 2H), 7.58 (t of d,J$_a$=2 Hz, J$_b$=7.8 Hz, 1H), 8.45 (d,J=5.4 Hz, 1H) ppm.

EXAMPLE 2

(±)-cis,trans-2-[N-acetyl-N-[[[(2-octadecyloxytetrahydrofuran-4-yl)methoxy]carbonyl]amino]methyl]pyridine.

To a cooled solution (0° C.) of the compound prepared in example 1c (2.8 g, 5.5 mmol) in dichloromethane (10 mL) was added acetyl chloride (0.4 mL) and the mixture was stirred at room temperature for 18 hours. Triethylamine (1.2 mL) was added, the solvents were removed and the resulting crude was purified by chromatography (silica gel, hexane:ethyl acetate 40%). The title compound of this example was obtained as a white solid (39% yield).

R$_f$=0.29 and 0.39 (cis and trans isomers, SG, hexane:ethyl acetate 1:1)

IR(KBr) $\nu$: 2911, 2846, 1732, 1693, 1588, 1430, 1391, 1372, 1343, 1222 cm$^{-1}$ $^1$H NMR (80 MHz, CDCl$_3$) $\delta$ (TMS): 0.87 (m, 3H), 1.26 (m, 37H), 2.5 (m, 1H), 2.62 (s, 3H), 3.3-4.3 (complex signal, 6H), 5.00 (m, 1H), 5.07 (s, 2H), 7.14 (m, 2H), 7.60 (t of d,Ja=7.2 Hz, Jb=1.6 Hz, 1H), 8.5 (d of t, Ja=4.8 Hz, Jb=0.9 Hz, 1H) ppm.

EXAMPLE 3

(±)-cis,trans-1-methyl-2-[N-acetyl-N-[[[(2-octadecyloxytetrahydrofuran-4-yl)methoxy]carbonyl]amino]methyl]pyridinium iodide.

A mixture of the compound prepared in example 2 (0.240 g), methyl iodide (1 mL) and acetonitrile (2 mL) was heated to reflux under argon during 18 hours. After cooling, the solvents were removed under vacuum and the residue recrystallized in dichloromethane and diethyl ether, yielding 0.2 g of the title compound of this example as a yellow solid (64% yield).

mp: 52.2°–60.8° C.

IR(KBr) $\nu$: 3440, 2913, 2846, 1744, 1677, 1626, 1510, 1429, 1347, 1210, 1083 cm$^{-1}$

Analysis calculated for $C_{33}H_{57}IN_2O_5 \cdot H_2O$: C 56.0%; H 8.4%; N 3.9%.

Found: C 56.01%; H 8.36%; N 3.91%

EXAMPLE 4

(±)-cis,trans-1-ethyl-2-[N-acetyl-N-[[[(2-octadecyloxytetrahydrofuran-4-yl)methoxy]carbonyl]amino]methyl]pyridinium iodide.

Following the procedure described in example 3 but using ethyl iodide instead of methyl iodide, the title compound of this example was obtained as a yellow solid (66% yield).

mp: 61.9°–81.1° C.

IR(KBr) $\nu$: 3440, 2913, 2846, 1737, 1682, 1625, 1579, 1508, 1463, 1212 cm$^{-1}$.

$^1$H NMR (80 MHz, CDCl$_3$) $\delta$ (TMS): 0.87 (m, 3H) 1.25 (m, 37H), 1.73 (t, J=7.2 Hz, 3H), 2.64 (s, 3H), 2.7 (m, 1H), 3.3–4.5 (complex signal, 6H), 5.05 (m, 3H), 5.43 (s, 2H), 7.73 (d, J=8.2 Hz, 1H), 8.04 (t, J=8.2 Hz, 1H), 8.45 (t, J=8 Hz, 1H), 9.61 (d, J=6Hz, 1H) ppm.

Analysis calculated for $C_{34}H_{59}IN_2O_5 \cdot 1.5H_2O$: C 56.0%; H 8.5%; N 3.8%.

Found: C 55.77%; H 8.31%; N 3.85%.

EXAMPLE 5

(±)-cis,trans-1-ethyl-2-[N-acetyl-N-[[[(2-octadecyloxytetrahydrofuran-4-yl)methoxy[carbonyl[amino]methyl]pyridinium chloride.

The compound prepared in example 4 (0.7 g) was treated with the ionic interchange resin IRA-410 (Cl$^-$) and eluted with methanol/water 7/3. The resulting chloride salt was recrystallized in acetone affording the title compound of this example as a white solid (61% yield).

mp: 53.8°–57.1° C.

IR(KBr) $\nu$: 3427, 2914, 2846, 1744, 1677, 1625, 1463, 1370, 1351 cm$^{-1}$.

$^1$H NMR (80 MHz, CDCl$_3$) $\delta$ (TMS): 0.88 (m, 3H) 1.26 (m, 37H), 1.74 (t, J=7.2 Hz, 3H), 2.64 (s, 3H), 3.3–4.5 (complex signal, 6H), 5.10 (m, 1H), 5.24 (q, J=7.2 Hz, 2H), 5.42 (s, 2H), 7.61 (d, J=6.7 Hz, 1H), 8.04 (t, J=5.8 Hz, 1H), 8.39 (t, J=6.6 Hz), 10.18 (d, J=6.0 Hz, 1H) ppm Analysis calculated for $C_{34}H_{59}ClN_2O_5 \cdot 1.5H_2O$: C 64.0%; H 9.7%; N 4.4%; Cl 5.9%.

Found: C 64.13%; H 10.02%; N 4.38%; Cl 5.6%.

EXAMPLE 6

(±)-cis,trans-2-[N-[[[(2-hexadecyloxytetrahydrofuran-4-yl)methoxy]carbonyl]amino]methyl]pyridine.

(a)(±)-cis,trans-(2-hexadecyloxytetrahydrofuran-4-yl)methanol Following the procedure described in example 1b but using hexadecanol instead of octadecanol, the title compound of this example was obtained as a 1:1 mixture of cis and trans isomers (45% yield).

IR(KBr) $\nu$: 3441, 2919, 2848, 1462, 1093 cm$^{-1}$.

(b) Preparation of the title compound of this example.

Following the procedure described in example 1c but using the compound prepared in example 6a instead of the compound prepared in example 1b, the title compound of this example was obtained as a white solid (90% yield).

$R_f$=0.18 (SG, hexane:ethyl acetate 1:1)

IR(KBr) $\nu$: 3197, 2913, 2844, 1714, 1592, 1551, 1462, 1434, 1277, 1255 cm$^{-1}$.

EXAMPLE 7

(±)-cis,trans-2-[N-acetyl-N-[[[(2-hexadecyloxytetrahydrofuran-4-yl)methoxy]carbonyl]amino]methyl]pyridine.

Following the procedure described in example 2 but using the compound prepared in example 6b instead of that prepared in example 1c, the title compound of this example was obtained as a white solid (40% yield).

$R_f$=0.43 and 0.48 (cis and trans isomers, SG, hexane:ethyl acetate 1:1)

IR(KBr) $\nu$: 2923, 2849, 1739, 1700, 1589, 1431, 1391, 1367, 1206 cm$^{-1}$.

$^1$H NMR (80 MHz, CDCl$_3$) $\delta$ (TMS): 0.87 m, 3H), 1.26 (m, 33H), 2.5 (m, 1H), 2.62 (s, 3H), 3.3–4.3 (complex signal, 6H), 5.00 (m, 1H), 5.07 (s, 2H), 7.14 (m, 2H), 7.60 (t of d, $J_a$=7.2 Hz, $J_b$=1.6 Hz, 1H), 8.50 (d of t, $J_a$=4.8 Hz, $J_b$=0.9 Hz, 1H) ppm.

EXAMPLE 8

(±)-cis,trans-1-ethyl-2-[N-acetyl-N-[[[(2-hexadecyloxytetrahydrofuran-4-yl)methoxy]carbonyl]amino]methyl]pyridinium iodide.

Following the procedure described in example 3 but using the compound prepared in example 7 instead of the compound prepared in example 2, and ethyl iodide instead of methyl iodide, the title compound of this example was obtained as a yellowish white solid (53% yield).

mp: 74.6°–79.9° C.

IR(KBr) $\nu$: 3430, 2912, 2846, 1743, 1693, 1624, 1464, 1446, 1369, 1350, 1211 cm$^{-1}$.

$^1$H NMR (80 MHz, CDCl$_3$) $\delta$ (TMS): 0.86 (m, 3H), 1.26 (m, 33H), 1.74 (t, J=7.2 Hz, 3H), 2.65 (s, 3H), 2.71 (m, 1H), 3.3–4.5 (complex signal, 6H), 5.08 (m, 3H), 5.45 (s, 2H), 7.75 (d, J=8.2 Hz, 1H), 8.05 (t, J=8.2 Hz 1H), 8.46 (t, J=8.0 Hz, 1H), 9.63 (d, J=6.0 Hz 1H) ppm.

Analysis calculated for $C_{32}H_{55}IN_2O_5 \cdot 0.5H_2O$: C 56.2%; H 8.2%; N 4.0%.

Found: C 56.04%; H 8.18%; N 4.04%.

EXAMPLE 9

(±)-cis,trans-2-[N-[[[(2-ethoxytetrahydrofuran-4-yl)methoxy]carbonyl]amino]methyl]pyridine (a)(±)-cis,trans-(2-ethoxytetrahydrofuran-4-yl)methyl phenyl carbonate.

To a cooled solution (ice bath) of the compound prepared in example 1a (2.4 g, 12.6 mmol) in dichloromethane (25 mL) was added, under argon, pyridine (1.2 mL) and phenyl chloroformate (1.1 mL). The mixture was stirred 1 hour at 0° C., diluted with dichloromethane, washed with cold water and dried over anhydrous sodium sulfate, affording 3.4 g of crude. The title compound was isolated by chromatography (silica gel, hexane:ethyl acetate 35%) as a colorless oil (1 g, 32% yield).

IR(film) $v$: 3041, 2973, 2895, 1758, 1589, 1490, 1442, 1370, 1343, 1247 cm$^{-1}$.

$^1$H NMR (80 MHz, CDCl$_3$) δ (TMS): 1.21 (t, J =6.7 Hz, 3H), 2.10 (m, 2H), 2.8 (m, 1H), 3.3–4.4 (complex signal, 6H), 5.15 (m, 1H), 7.22 (m, 5H) ppm.

(b) Preparation of the title compound of this example.

Following the procedure described in example 1c, the compound prepared in example 9a was treated with 2-aminomethylpyridine, affording the title compound of this example as a colorless oil (quantitative yield).

R$_f$=0.15 (SG, hexane:ethyl acetate 1:1)

IR(film) $v$: 3324, 3050, 2971, 1714, 1589, 1524, 1471, 1433, 1244, 1051 cm$^{-1}$.

$^1$H NMR (80 MHz, CDCl$_3$) δ (TMS): 1.18 (t, J=7.0 Hz, 3H), 2.0 (m, 2H), 2.2 (m, 1H), 3.2–4.3 (complex signal, 6H), 4.48 (d, J=5.4 Hz, 2H), 5.15 (m, 1H), 7.27 (m, 2H), 7.7 (t of d, J$_a$=7.8 Hz, J$_b$=2.0 Hz, 1H), 8.52 (d, J=5.4 Hz, 1H) ppm.

EXAMPLE 10

(±)-cis,trans-2-[N-acetyl-N-[[[(2-ethoxytetrahydrofuran-4-yl)methoxy]carbonyl]amino]methyl]pyridine Following the procedure described in example 2, but using the compound prepared in example 9b instead of the one prepared in example 1c, the title compound was obtained as a white solid (45% yield)

R$_f$: 0.19 (SG, hexane:ethyl acetate 1:1)

IR(KBr) $v$: 2927, 1737, 1700, 1589, 1429, 1367, 1205 cm$^{-1}$.

$^1$H NMR (80 MHz, CDCl$_3$) δ (TMS): 1.49 (t, J=7.0 Hz, 3H), 2.0 (m, 2H), 2.62 (s, 3H), 3.2–4.4 (complex signal, 6H), 5.0 (m, 1H), 5.07 (s, 2H), 7.14 (m, 2H), 7.63 (t of d, J$_a$=7.2 Hz, J$_b$=1.6 Hz, 1H), 8.53 (d, J=4.8 Hz, 1H) ppm.

EXAMPLE 11

(±)-cis,trans-1-ethyl-2-[N-acetyl-N-[[[(2-ethoxytetrahydrofuran-4-yl) methoxy]carbonyl]amino]methyl]pyridinium iodide.

Following the procedure described in example 3 but using the compound described in example 10 and ethyl iodide as a reagent, the title compound was obtained as a yellowish white solid (15% yield)

mp: 96.6°–105.5° C.

IR(KBr) $v$: 3457, 2964, 1743, 1692, 1622, 1509, 1370, 1350, 1212 cm$^{-1}$ $^1$H NMR (80 MHz, CDCl$_3$) δ (TMS): 1.15 t, J=7.05 Hz, 3H), 1.73 (t, J=7.2 Hz, 3H), 2.0 (m, 2H), 2.65 (s, 3H), 2.70 (m, 1H), 3.3–4.1 (complex signal, 4H), 4.33 (dd, J$_a$=9.77 Hz, J$_b$=7.05 Hz, 2H), 5.05 (m, 3H), 5.45 (s, 2H), 7.91 (d, J=8.3 Hz, 1H), 8.10 (t, J=7.0 Hz, 1H), 8.61 (t, J=7.9 Hz, 1H), 9.59 (d, J=6.1 Hz, 1H)

Analysis calculated for C$_{18}$H$_{27}$IN$_2$O$_5$: C 45.2%; N 5.6% H; 5.8%.

Found: C 45.52%; H 5.81%; N 5.83%.

EXAMPLE 12

(±)-cis,trans-2-[N-[[[(2-(3-methylbutoxy)tetrahydrofuran-4-yl)methoxy]carbonyl]amino]methyl]pyridine.

(a)(±)-cis,trans-[2-(3-methylbutoxy)tetrahydrofuran-4-yl]methanol. Following the procedure described in example 1b, but using 3-methylbutanol instead of octadecanol, the title compound of this example was obtained as a colorless oil (63% yield)

IR (film) $v$: 3419, 2952, 1462, 1365, 1313 cm$^{-1}$.

$^1$H NMR (80 MHz, CDCl$_3$) δ (TMS): 0.86 (s, 3H), 0.93 (s, 3H), 1.5 (m, 3H), 2.48 (m, 1H), 2.74 (s, 1H), 3.44 (m, 6H), 5.09 (d, J =4.9 Hz, 1H) ppm.

(b) Preparation of the title compound of this example.

Following the procedure described in example 1c but using the compound prepared in example 12a instead of the compound prepared in example 1b, the title compound of this example was obtained as a colorless oil (60% yield)

IR (film) $v$: 3333, 3049, 2953, 1714, 1590, 1566, 1525, 1464 cm$^{-1}$ $^1$H NMR (80 MHz, CDCl$_3$) δ (TMS): 0.85 (s, 3H), 0.93 (s, 3H), 1.46 (m, 3H), 2.68 (m, 1H), 3.3–4.3 (m, 6H), 4.47 (d, J =5.5 Hz, 2H), 5.06 (m, 1H), 6.10 (m, 1H, NH), 7.25 (m, 2H), 7.66 (t of d, J$_a$=7.7 Hz, J$_b$=1.9 Hz, 1H), 8.53 (d, J=4.4 Hz, 1H) ppm.

EXAMPLE 13

(±)-cis,trans-2-[N-acetyl-N-[[[2-(3-methylbutoxy)tetrahydrofuran-4-yl) methoxy]carbonyl]amino]methyl]pyridine.

Following the procedure described in example 2 but using the compound prepared in example 12b instead of the one prepared in example 1c, the title compound of this example was prepared as a colorless oil (64.5% yield).

IR (film) $v$: 2952, 2869, 1737, 1697, 1589, 1430, 1391, 1366, 1346, 1205 cm$^{-1}$ $^1$H NMR (80 MHz, CDCl$_3$) δ (TMS): 0.84 (s, 3H), 0.92 (s, 3H), 1–2 (m, 5H), 2.29 (m, 1H), 2.62 (s, 3H), 3.6 (m, 4H), 4.14 (m, 2H), 4.97 (m, 1H), 5.07 , (s, 2H), 7.18 (m, 2H), 7.62 (t of d, J$_a$=7.7 Hz, J$_b$=1.8 Hz, 1H) 8.5 (d, J$_a$=4.6 Hz, 1H) ppm.

EXAMPLE 14

(±)-cis,trans-1-ethyl-2-[N-acetyl-N-[[[(2-(3-methylbutoxy)tetrahydrofuran-4-yl) methoxy]carbonyl]amino]methyl]pyridinium iodide.

Following the procedure described in example 3 but using the compound prepared in example 13 instead of the one prepared in example 2, and ethyl iodide instead of methyl iodide as a reagent, the title compound of this example was obtained as a yellowish white solid (35% yield).

mp: 57.9°–68.6° C.

$^1$H NMR (80 MHz, CDCl$_3$) δ (TMS): 0.85 (s, 3H), 1.65 (m, 7H), 2.65 (s, 3H), 2.66 (m, 1H), 3.7 (m, 4H), 4.35 (t, J=7.4 Hz, 2H), 5.08 (m, 3H), 5.45 (m, 2H), 7.83 (d, J=7.8 Hz, 1H), 8.08 (t, J=7.1 Hz, 1H), 8.54 (t, J=8.0 Hz, 1H), 9.62 (d, J=5.9 Hz, 1H) ppm.

Analysis calculated for $C_{21}H_{33}IN_2O_5 \cdot H_2O$: C 46.8%; H 6.5%; N 5.2%.
Found: C 46.82%; H 6.16%; N 5.30%.

EXAMPLE 15

(±)-cis,trans-2-[N-[[[(2-(3-phenylpropoxy)tetrahydrofuran-4-yl)methoxy]carbonyl]amino]methyl]pyridine.

(a)(±)-cis,trans-[2-(3-phenylpropoxy)tetrahydrofuran-4-yl]methanol.

Following the procedure described in example 1b, but using 3-phenyl-1-propanol instead of octadecanol, the title compound was obtained as a colorless oil (49% yield).

IR (film) ν: 3403, 3080, 3056, 3021, 2937, 1492, 1441, 1343, 1051 cm$^{-1}$.

$^1$H NMR (80 MHz, CDCl$_3$) δ (TMS): 1.16 (t, J =7.3 Hz, 2H), 1.8 (m, 2H), 2.40 (m, 1H), 2.63 (m, 2H), 3.2–3.9 (m, 6H), 5.08 (m, 1H), 7,18 (m, 5H) ppm.

(b) Preparation of the title compound of this example.

Following the procedure described in example 1c, but using the compound prepared in example 15a instead of the one prepared in example 1b, the title compound of this example was obtained as a colorless oil (70% yield).

IR (film) ν: 3329, 2943, 1714, 1524, 1244, 1094 cm$^{-1}$ $^1$H NMR (80 MHz, CDCl$_3$) δ (TMS): 1.17 (t, J =6.9 Hz, 2H), 1.75 (m, 3H), 2.61 (m, 2H), 3.4–4.3 (m, 6H), 4.46 (d, J =5.5 Hz, 2H), 5.10 (m, 1H), 6.01 (m, 1H), 7.21 (m, 7H), 7.65 (t, J=7.7 Hz, 1H), 8.52 (d, J=4.6 Hz, 1H) ppm.

EXAMPLE 16

(±)-cis,trans-2-[N-acetyl-N-[[[(2-(3-phenylpropoxy)tetrahydrofuran-4-yl) methoxy]carbonyl]amino]methyl]pyridine.

Following the procedure described in example 2, but using the compound prepared in example 15b instead of the one prepared in example 1c, the title compound of this example was obtained as a colorless oil (39% yield).

IR (film) ν: 3080, 3057, 2943, 1735, 1700, 1589, 1472, 1429, 1367, 1286, 1205, 1043 cm$^{-1}$ $^1$H NMR (80 MHz, CDCl$_3$) δ (TMS): 1.4–1.9 (m, 4H), 2.62 (t, J=6.2 Hz, 2 H), 2.62 (s, 3H), 3.37 (m, 2H), 4.06 (m, 2H), 4.98 (m, 1H), 5.06 (s, 2H), 7.13 (m, 7H), 7.60 (t, J =8.6 Hz, 1H), 8.48 (d, J =4.9 Hz, 1H) ppm

EXAMPLE 17

(±)-cis,trans-1-ethyl-2-[N-acetyl-N-[[[(2-(3-phenylpropoxy)tetrahydrofuran-4-yl)methoxy]carbonyl]amino]methyl]pyridinium iodide.

Following the procedure described in example 3 but using the compound prepared in example 16 instead of the one prepared in example 2, and ethyl iodide instead of methyl iodide as a reagent, the title compound of this example was obtained as a yellowish white solid (44% yield).

mp: 67.1°–72.9° C.

IR(KBr) ν: 3440, 3020, 2939, 1744, 1692, 1622, 1369, 1349, 1212 cm$^{-1}$

Analysis calculated for $C_{25}H_{33}IN_2O_5 \cdot H_2O$: C 51.2%; H 5.9%; N 4.8%.
Found: C 51.32%; H 5.79%; N 4.82%.

We claim:

1. 4-Substituted 2-alkoxytetrahydrofuran derivatives of formula I

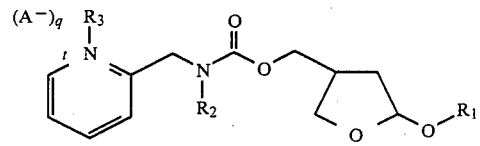

wherein:
— $R_1$ is a linear or branched alkyl, alkenyl or alkynyl group, of 1 to 24 carbon atoms, or a phenyl-($C_1$-$C_4$)alkyl group;
— $R_2$ is hydrogen, $C_1$-$C_4$-acyl or $C_1$-$C_4$-alkoxycarbonyl;
— $R_3$ is either an electron pair, in which case t means nothing and q is zero, or $R_3$ is hydrogen or $C_1$-$C_4$alkyl, in which case t is (+) and q=1;
— A— is a pharmaceutically acceptable anion.

2. A compound according to claim 1 wherein:
— $R_1$ is n-($C_{12}$-$C_{20}$)alkyl, linear or branched ($C_1$-$C_6$)alkyl, or phenyl-n-($C_2$-$C_4$)alkyl;
— $R_2$ is hydrogen or $C_1$-$C_3$-acyl;
— $R_3$ is hydrogen or $C_1$-$C_4$ alkyl;
— t is (+) and q=1;
— A— is chloride, bromide, or iodide.

3. A compound according to claim 2 wherein:
— $R_1$ is n-($C_{16}$-$C_{18}$)alkyl, linear or branched ($C_2$-$C_5$)alkyl, or phenyl-n-($C_2$-$C_4$)alkyl;
— $R_2$ is $C_1$-$C_3$-acyl;
— $R_3$ is $C_1$-$C_4$ alkyl;
— t is (+) and q=1;
— A— is chloride or iodide.

4. A compound according to claim 3 wherein:
— $R_1$ is n-($C_{16}$-$C_{18}$)alkyl, linear or branched ($C_2$-$C_5$)alkyl, or phenyl-n-($C_2$-$C_4$)alkyl;
— $R_2$ is acetyl;
— $R_3$ is ethyl;
— t is (+) and q=1;
— A— is chloride or iodide.

5. A compound according to claim 4 which is (±)-cis,trans-1-ethyl-2-[N-acetyl-N-[[[2-octadecyloxytetrahydrofuran-4-yl)methoxy]carbonyl]amino]methyl]pyridinium chloride.

6. A compound according to claim 4 which is (±)-cis,trans-1-ethyl-2-[N-acetyl-N-[[[2-hexadecyloxytetrahydrofuran-4-yl)methoxy]carbonyl]amino]methyl]pyridinium iodide.

7. A compound according to claim 4 which is (±)-cis,trans-1-ethyl-2-[N-acetyl-N-[[[2-ethoxytetrahydrofuran-4-yl) methoxy] carbonyl] amino] methyl] pyridinium iodide.

8. A compound according to claim 4 which is (±)-cis,trans-1-ethyl-2-[N-acetyl-N-[[[2-(3-methylbutoxy)tetrahydrofuran-4-yl) methoxy] carbonyl] amino]methyl]pyridinium iodide.

9. A compound according to claim 4 which is (±)-cis,trans1-ethyl-2-[N-acetyl-N-[[[2-(3-phenylpropoxy)tetrahydrofuran-4-yl) methoxy] carbonyl] amino]methyl]pyridinium iodide.

10. A pharmaceutical composition which comprises an effective amount of a compound of formula I in association with a pharmaceutically acceptable carrier, excipient or diluent therefor.

11. A method for treating a patient suffering from a PAF-mediated illness which comprises administering to said patient an effective dose of a compound of formula I in combination with a pharmaceutically acceptable excipient.

* * * * *

UNITED STATES PATENT AND TRADEMARK OFFICE
CERTIFICATE OF CORRECTION

PATENT NO.   : 4,980,362

DATED        : December 25, 1990

INVENTOR(S)  : Elena CARCELLER and Javier BARTROLI

It is certified that error appears in the above-identified patent and that said Letters Patent is hereby corrected as shown below:

Column 18, line 56, delete "trans1" and substitute therefor --trans-1--.

Signed and Sealed this

Eleventh Day of August, 1992

Attest:

DOUGLAS B. COMER

Attesting Officer

Acting Commissioner of Patents and Trademarks